United States Patent
Kim et al.

(10) Patent No.: US 10,994,121 B2
(45) Date of Patent: *May 4, 2021

(54) CARBON NANOTUBE COMPOSITE ELECTRODE USING VACUUM SUCTION

(71) Applicant: Industry-Academic Cooperation Foundation, Chosun University, Gwangju (KR)

(72) Inventors: Youn Tae Kim, Daejeon (KR); Jae Hyo Jung, Gwangju (KR); Ji Hoon Lee, Gwangju (KR); Si Ho Shin, Gwangju (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 805 days.

This patent is subject to a terminal disclaimer.

(21) Appl. No.: 15/848,545

(22) Filed: Dec. 20, 2017

(65) Prior Publication Data
US 2019/0105485 A1    Apr. 11, 2019

(30) Foreign Application Priority Data

Oct. 11, 2017   (KR) .......................... 10-2017-0129839

(51) Int. Cl.
*A61B 5/0408*   (2006.01)
*A61B 5/0478*   (2006.01)
(Continued)

(52) U.S. Cl.
CPC ............ *A61N 1/042* (2013.01); *C01B 32/168* (2017.08); *C08L 83/04* (2013.01); *C09J 183/04* (2013.01);
(Continued)

(58) Field of Classification Search
CPC . A61B 5/0006; A61B 5/04004; A61B 5/0478; A61B 5/0492; A61B 5/6834; A61B 2562/0209; A61B 2562/16; A61B 2562/125; A61B 1/042; A61B 1/0472; C08L 83/04; C08L 83/14; C08L 83/00;
(Continued)

(56) References Cited

U.S. PATENT DOCUMENTS 4,637,399 A * 1/1987 Asai .................... A61B 5/04286
                                                                    600/387
2017/0209097 A1* 7/2017 Kang ................... A61B 5/6834

FOREIGN PATENT DOCUMENTS

KR           101037405 B1 *  5/2011  ......... A61B 5/04082
KR    10-2017-0100956 A      9/2017

* cited by examiner

*Primary Examiner* — Eun Hwa Kim
(74) *Attorney, Agent, or Firm* — Renner, Otto, Boisselle & Sklar, LLP

(57) ABSTRACT

A Carbon NanoTube (CNT) composite electrode includes a lower electrode having a through-hole formed therein, and configured to be attached to the skin of a subject body to detect a biosignal, an upper electrode provided on one surface of the lower electrode to form an enclosed space between the lower electrode and the upper electrode, and configured to receive the biosignal detected by the lower electrode, and an air discharge portion formed in at least one of the lower electrode and the upper electrode, and discharging air present in the enclosed space and the through-hole externally so as to be configured to allow the upper electrode and the lower electrode to be attached to the skin of the subject body via vacuum suction.

10 Claims, 8 Drawing Sheets

(51) Int. Cl.
*A61N 1/04* (2006.01)
*C01B 32/168* (2017.01)
*C09J 183/04* (2006.01)
*C08L 83/04* (2006.01)
A61B 5/0492 (2006.01)
A61B 5/04 (2006.01)
A61B 5/00 (2006.01)
C08L 83/14 (2006.01)
C08G 77/20 (2006.01)
C08G 77/50 (2006.01)

(52) U.S. Cl.
CPC .......... *A61B 5/0006* (2013.01); *A61B 5/04004* (2013.01); *A61B 5/0408* (2013.01); *A61B 5/0478* (2013.01); *A61B 5/0492* (2013.01); *A61B 2562/0209* (2013.01); *A61N 1/0472* (2013.01); *C08G 77/20* (2013.01); *C08G 77/50* (2013.01); *C08L 83/14* (2013.01)

(58) Field of Classification Search
CPC ...... C01B 32/168; C09J 183/04; C08G 77/20; C08G 77/50; C08K 5/56
See application file for complete search history.

A-A'

CARBON NANOTUBE COMPOSITE ELECTRODE USING VACUUM SUCTION

CROSS-REFERENCE TO RELATED APPLICATION

This application claims the benefit of priority to Korean Patent Application No. 10-2017-0129839, filed on Oct. 11, 2017 with the Korean Intellectual Property Office, the entirety of which is incorporated herein by reference.

BACKGROUND

The present disclosure relates to a carbon nanotube (CNT) composite electrode using vacuum suction.

The present disclosure has been derived from research [Assignment Management number: 1711055214, title: energy harvesting for wearable device and wireless power transmitting technique] conducted as part of a research development high quality man resource support project by the Institute for Information & Communications Technology Promotion and the Ministry of Science and ICT of Korea.

An electrode attached to a body is commonly used for measuring various electrical signals generated from a body such as an electrocardiogram (ECG), an electromyograph (EMG), bio-impedance, and the like.

Such an electrode is usually divided into one of a wet-type electrode or a dry-type electrode.

Typically, there is provided a disposable wet-type Ag/AgCl electrode containing hydrogel and an adhesive material. The disposable wet-type Ag/AgCl electrode is most often used for measuring a biosignal due to ease of attachment to the body of a patient and high electrical properties. However, it is difficult to measure a biosignal for an elongated period of time because electrical characteristics may be changed over time and a problematic reaction, such as an allergic reaction, may be caused during measurement for an elongated period of time.

A dry-type electrode is fixed to a body using a separate tool such as a band, or an electrode is fixed to the skin of a user using a clamping shape or an adsorption method. However, since a volume of an electrode may be significantly large, movement in an attached state may be significantly limited.

SUMMARY

An aspect of the present disclosure provides a carbon nanotube (CNT) composite electrode attached to the skin of a subject body without any tools or adhesives, maintaining adhesion of an electrode by significantly reducing a space due to a wrinkle in the skin of a subject body, and preventing skin troubles which occur during elongated measurement simultaneously.

According to an aspect of the present disclosure, a Carbon NanoTube (CNT) composite electrode includes: a lower electrode having a through-hole formed therein, and configured to be attached to the skin of a subject body to detect a biosignal; an upper electrode provided on one surface of the lower electrode to form an enclosed space between the lower electrode and the upper electrode, and configured to receive the biosignal detected by the lower electrode; and an air discharge portion formed in at least one of the lower electrode and the upper electrode, and discharging air present in the enclosed space and the through-hole externally so as to be configured to allow the upper electrode and the lower electrode to be attached the skin of a subject body via vacuum suction.

BRIEF DESCRIPTION OF DRAWINGS

The above and other aspects, features, and advantages of the present disclosure will be more clearly understood from the following detailed description taken in conjunction with the accompanying drawings, in which.

DETAILED DESCRIPTION

Figure 1A:
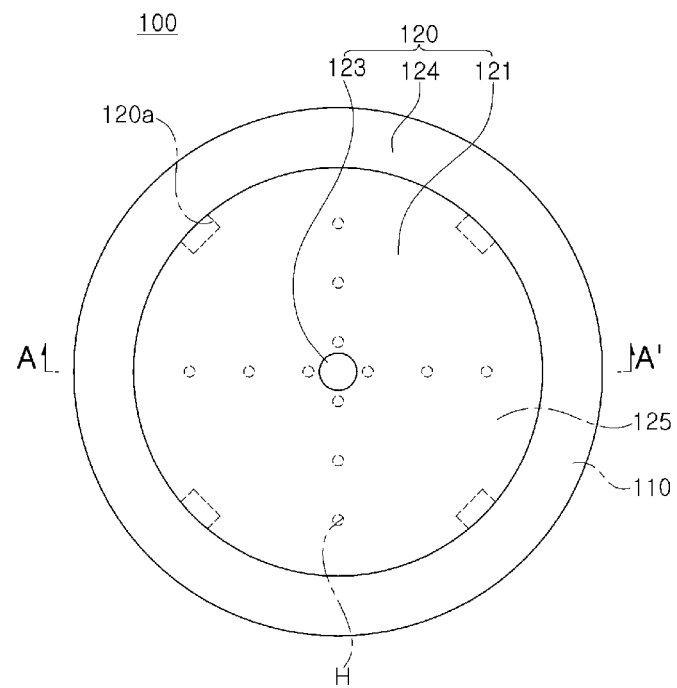
FIGS. 1A through 1F are views illustrating a CNT composite electrode using vacuum suction according to an exemplary embodiment.

Hereinafter, embodiments of the present disclosure will be described as follows with reference to the attached drawings.

The present disclosure may, however, be exemplified in many different forms and should not be construed as being limited to the specific embodiments set forth herein. Rather, these embodiments are provided so that this disclosure will be thorough and complete, and will fully convey the scope of the disclosure to those skilled in the art.

Throughout the specification, it will be understood that when an element, such as a layer, region or wafer (substrate), is referred to as being 'on,' 'connected to,' or 'coupled to' another element, it can be directly 'on,' 'connected to,' or 'coupled to' the other element or other elements intervening therebetween may be present. In contrast, when an element is referred to as being 'directly on,' 'directly connected to,' or 'directly coupled to' another element, there may be no other elements or layers intervening therebetween. Like numerals refer to like elements throughout. As used herein, the term 'and/or' includes any and all combinations of one or more of the associated listed items.

It will be apparent that although the terms first, second, third, etc. may be used herein to describe various members, components, regions, layers and/or sections, any such members, components, regions, layers and/or sections should not be limited by these terms. These terms are only used to distinguish one member, component, region, layer or section from another region, layer or section. Thus, a first member, component, region, layer or section discussed below could be termed a second member, component, region, layer or section without departing from the teachings of the exemplary embodiments.

Spatially relative terms, such as 'above,' 'upper,' 'below,' and 'lower' and the like, may be used herein for ease of description to describe one element's relationship relative to another element(s) as shown in the figures. It will be understood that spatially relative terms are intended to encompass different orientations of the device in use or operation, in addition to the orientation depicted in the figures. For example, if the device in the figures is turned over, elements described as 'above,' or 'upper,' relative to other elements would then be oriented 'below,' or 'lower,' relative to the other elements or features. Thus, the term 'above' can encompass both the above and below orientations depending on a particular direction of the figures. The device may be otherwise oriented (rotated 90 degrees or at other orientations) and the spatially relative descriptors used herein may be interpreted accordingly.

The terminology used herein describes particular embodiments only, and the present disclosure is not limited thereby. As used herein, the singular forms 'a,' 'an,' and 'the' are intended to include the plural forms as well, unless the context clearly indicates otherwise. It will be further understood that the terms 'comprises,' and/or 'comprising' when used in this specification, specify the presence of stated features, integers, steps, operations, members, elements, and/or groups thereof, but do not preclude the presence or addition of one or more other features, integers, steps, operations, members, elements, and/or groups thereof.

Hereinafter, embodiments of the present disclosure will be described with reference to schematic views illustrating embodiments of the present disclosure. In the drawings, for example, due to manufacturing techniques and/or tolerances, modifications of the shape shown may be estimated. Thus, embodiments of the present disclosure should not be construed as being limited to the particular shapes of regions shown herein, for example, to include a change in shape resulting from manufacturing. The following embodiments may also be constituted alone, in combination or in partial combination.

The contents of the present disclosure described below may have a variety of configurations and propose only a required configuration herein, but are not limited thereto.

FIGS. 1A through 1F are drawings illustrating a carbon nanotube (CNT) composite electrode 100 using vacuum suction, according to an exemplary embodiment.

Figure 1B:
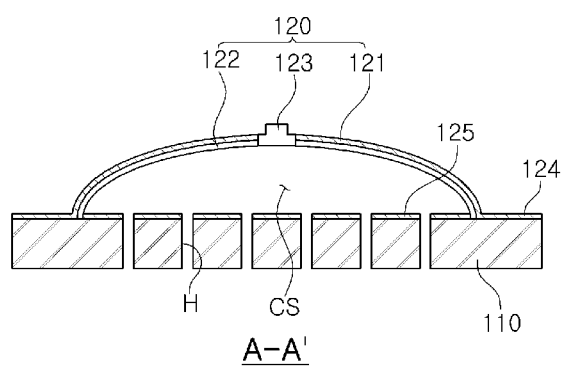
Figure 1C:
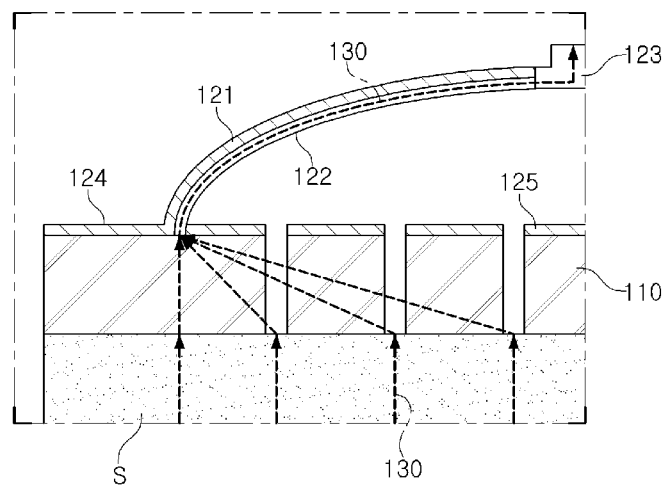
Figure 1D:
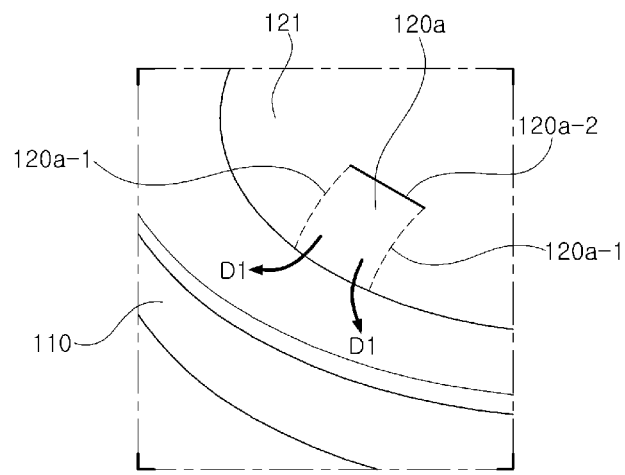
Figure 1E:
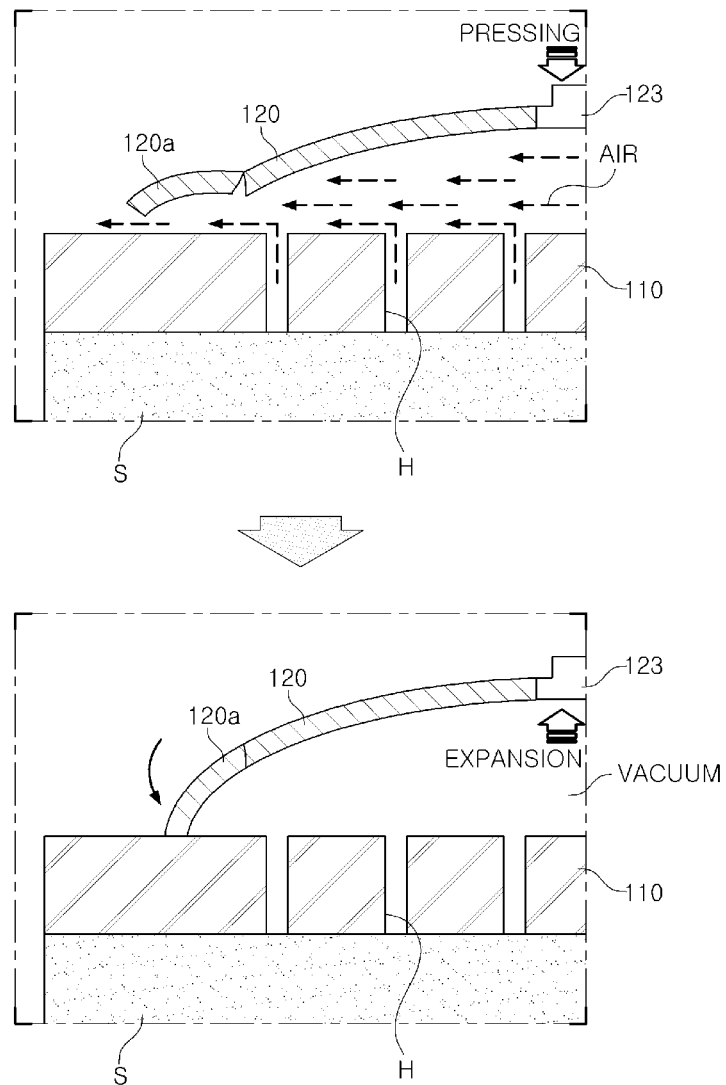
Figure 1F:
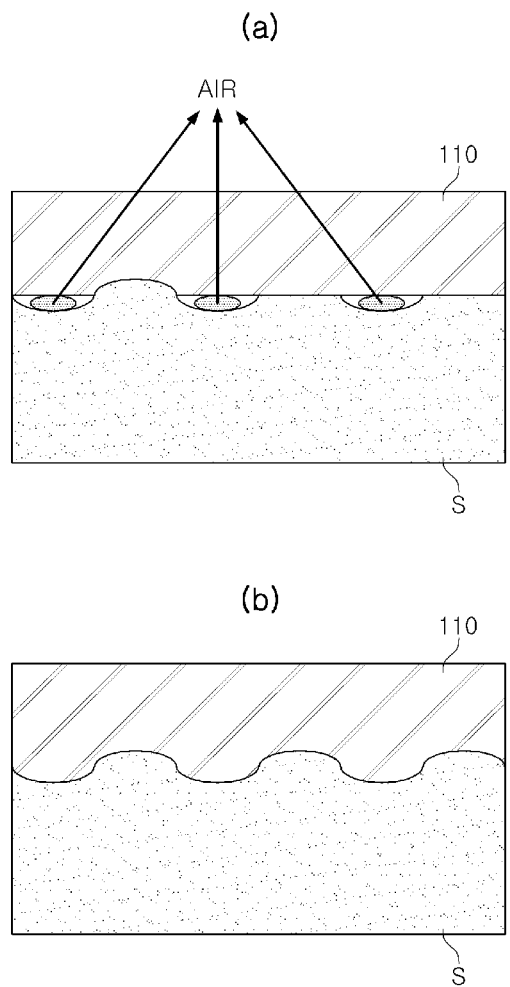

In detail, FIG. 1A is a view of a CNT composite electrode according to an exemplary embodiment as viewed from above, FIG. 1B is a view taken along line A-A' of FIG. 1A, FIG. 1C is a view illustrating a biosignal transmission process by a CNT composite electrode according to an exemplary embodiment, FIG. 1D is a view illustrating an air discharge portion formed in an upper electrode of FIG. 1A, FIG. 1E is a view illustrating an operation of the air discharge portion of FIG. 1D, and FIG. 1F is a view illustrating an adhesion state of a subject according to a material of a lower electrode of the CNT composite electrode according to an exemplary embodiment.

Hereinafter, referring to FIGS. 1A through 1F, a CNT composite electrode using vacuum suction according to an exemplary embodiment will be described in detail.

As illustrated in FIGS. 1A and 1B, the CNT composite electrode 100 using vacuum suction according to an exemplary embodiment may include a lower electrode 110 and an upper electrode 120.

The lower electrode 110 has a plurality of through-holes H formed to remove air between skin S of a subject body and the lower electrode 110 or the upper electrode 120, and is configured to be attached to the skin S of a subject body to detect a biosignal.

The lower electrode 110 is formed of a material having adhesion and conductivity, and may have a circular plate-shaped structure connected to a conductive layer 122 of the upper electrode 120, which will be described later. A shape of the lower electrode 110 described above is circular, and it is to be noted that various shapes such as a rectangular shape, and the like may be employed.

The material having adhesion and conductivity described above may include a mixed material of a Carbon nanotube (CNT) and adhesive PolyDiMethylSiloane (aPDMS).

FIG. 1F is a view illustrating a state of adhesion to the skin S of a subject body according to a material of the lower electrode 110 of the CNT composite electrode according to an exemplary embodiment. (a) of FIG. 1F illustrates the case in which a material of the lower electrode 110 is silicon, and (b) of FIG. 1F illustrates the case in which a material of the lower electrode 110 is aPDMS.

As illustrated in FIG. 1F, when the lower electrode 110 is formed of aPDMS, a space with respect to skin is significantly reduced, so adhesion between the lower electrode 110 and the skin S of a subject body may be increased.

Referring to FIGS. 1A and 1B again, the upper electrode 120 is provided on one surface of the lower electrode 110 to form an enclosed space CS with the lower electrode 110, and is configured to receive a biosignal detected by the lower electrode 110.

The upper electrode 120 described above may include an arcuate structure 121 formed of a material having elastic force and restoring force, the conductive layer 122 configured to be formed in an inner surface of the arcuate structure 121, and a snap connector 123 formed in an outer surface of the arcuate structure 121, and configured to pass through the arcuate structure 121 and to be connected to the conductive layer 122. Here, the material of the arcuate structure 121 having elastic force and restoring force may include, for example, silicon.

The conductive layer 122 may include a conductor with which the entirety or a portion of an inner surface of the arcuate structure 121 is coated using sputtering, or attached in the form of a conductive wire or a conductive tape. The conductive layer 122 may be connected to the snap connector 123 and the lower electrode 110.

The snap connector 123 may be used to transmit a biosignal externally and may be formed of a metal material. The snap connector 123 may have a button shape used in a wet type Ag/AgCl electrode according to the related art.

In addition, according to an exemplary embodiment, in one surface of a circular plate-shaped structure 110, an insulating layer 125 for preventing the conductive layer 122 of the upper electrode 120 and the circular plate-shaped structure 110 from being in contact with each other by external force may be further formed therein. In this regard, when the conductive layer 122 of the upper electrode 120 and the circular plate-shaped structure 110 are in contact with each other by external force having been applied, distortion and noise of a biosignal may be introduced.

Moreover, an insulating layer 124 may be further formed in one surface of the circular plate-shaped structure 110 to which the arcuate structure 121 is not attached. In this regard, an exposed portion of the circular plate-shaped structure 110 is covered, so noise generated from an external environment may be prevented.

Meanwhile, FIG. 1C is a view illustrating a biosignal transmission process due to a CNT composite electrode according to an exemplary embodiment.

As illustrated in FIG. 1C, a biosignal 130 of the skin S of a subject body may be transmitted to the snap connector 123 through the lower electrode 110 and the conductive layer 122 formed in an inner surface of the arcuate structure 121, of the upper electrode.

Meanwhile, according to an exemplary embodiment, the upper electrode 120 may include an air discharge portion

120a configured to allow the upper electrode 120 and the lower electrode 110 to be attached to the skin S of a subject body via vacuum suction, by discharging air present in the enclosed space CS and the through-hole H is externally. The air discharge portion 120a described above may be provided in an amount of at least two or more, as illustrated in FIG. 1A.

The air discharge portion 120a described above is illustrated in FIG. 1D.

Referring to FIG. 1D, the air discharge portion 120a may have a hinge structure. In other words, the air discharge portion 120a is a portion of the arcuate structure 121, has cut out portions 120a-1 in parallel in both sides, and may be open and restored in an outer direction D1 based on a hinge portion 120a-2, which is not cut. The air discharge portion 120a is formed in one side of the arcuate structure 121 in contact with the circular plate-shaped structure 110, and may be open in the outer direction D1 when external force is applied and may be restored in an original state when the external force is applied.

In FIG. 1E, an operating principle of the air discharge portion 120a according to an exemplary embodiment, described above, is illustrated.

As illustrated in FIG. 1E, when external force is applied and the upper electrode 120 (In detail, the snap connector 123) is pressed thereby, the air discharge portion 120a is open, so air inside an enclosed space (CS of FIG. 1B) may be discharged through the air discharge portion 120a, having been open, externally. Thereafter, when the external force is removed, the air discharge portion 120a is restored to an original state, so an interior of the enclosed space (CS of FIG. 1B) forms a vacuum. Thus, the upper electrode 120 and the lower electrode 110 may be attached to the skin S of a subject body via vacuum suction.

Figure 2A:
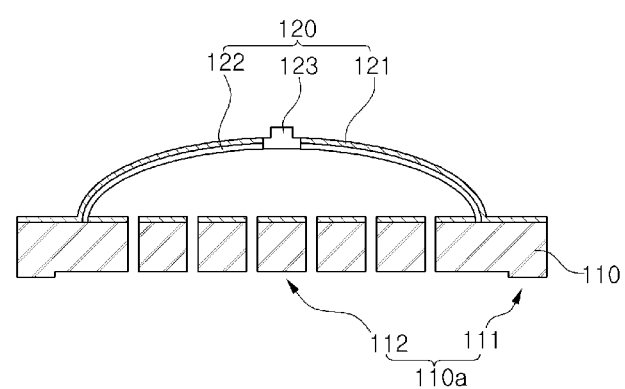
FIGS. 2A and 2B are views illustrating an air discharge portion formed in a lower electrode according to another exemplary embodiment and an operating principle thereof.
Figure 2B:
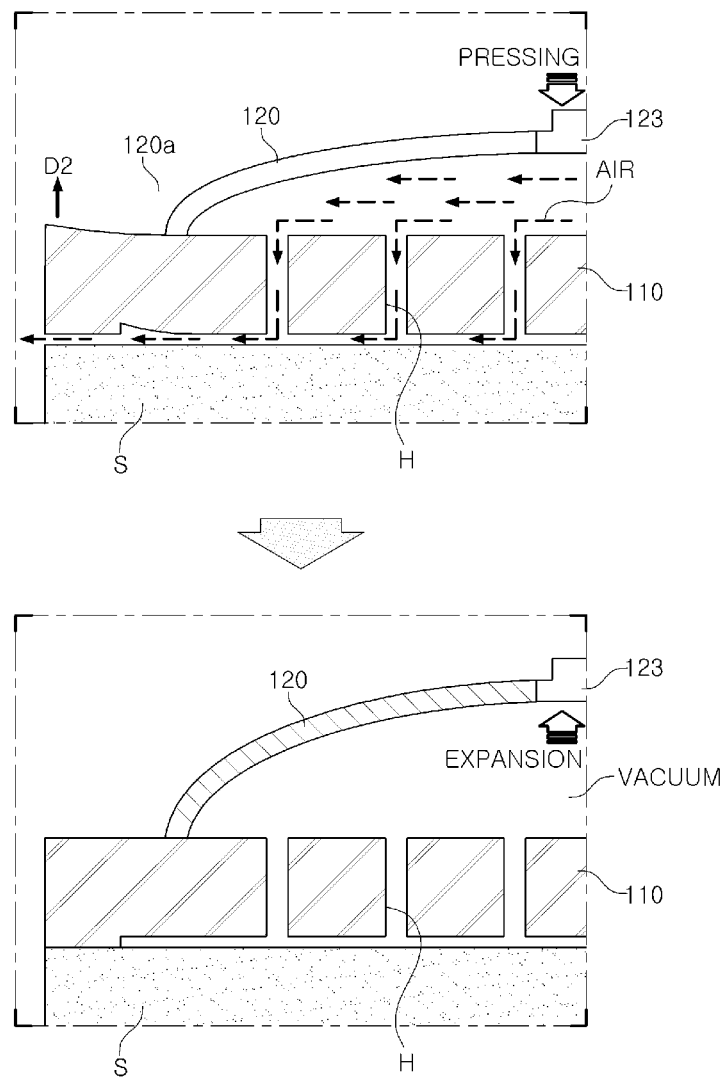

Meanwhile, FIGS. 2A and 2B are views illustrating an air discharge portion formed in a lower electrode according to another exemplary embodiment and an operating principle thereof.

In a different manner from an exemplary embodiment of FIG. 1A, an air discharge portion 110a illustrated in FIG. 2A is configured to be formed in the lower electrode 110.

In detail, the air discharge portion 110a is formed in one surface (a lower surface) of the circular plate-shaped structure 110 attached to the skin S of a subject body, and an outer portion 111 protrudes and a central portion 112 is concave.

The air discharge portion 110a according to another exemplary embodiment, described above, is operated as illustrated in FIG. 2B.

In detail, as illustrated in FIG. 2B, when external force is applied and the upper electrode 120 is pressed thereby, the outer portion 111 of the lower electrode 110 is lifted up in an upper direction D2, so air inside the enclosed space (CS of FIG. 1B) may be discharged externally. Thereafter, when the external force is removed, the outer portion 111 of the lower electrode 110 is restored to an original state, so an interior of the enclosed space (CS of FIG. 1B) forms a vacuum. Thus, the upper electrode 120 and the lower electrode 110 may be attached to the skin S of a subject body via vacuum suction.

Figure 3A:
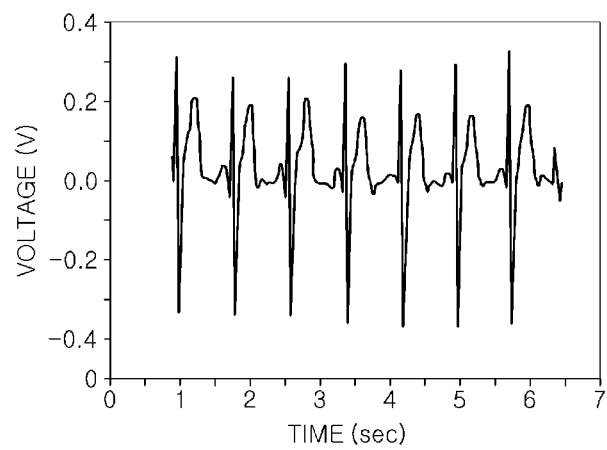
FIGS. 3A and 3B illustrates a comparative example of a biosignal measured using a wet-type electrode according to the related art and a CNT composite electrode according to an exemplary embodiment.
Figure 3B:
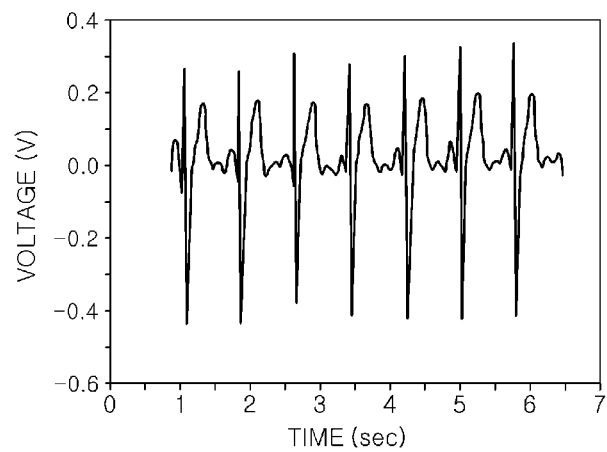

FIGS. 3A and 3B illustrate a comparative example of a biosignal measured by a wet-type electrode according to the related art and the CNT composite electrode according to an exemplary embodiment. FIG. 3A illustrates a biosignal measured by a commercialized wet-type electrode, and FIG. 3B illustrates a biosignal measured by a CNT composite electrode according to an exemplary embodiment.

As illustrated in FIGS. 3A and 3B, it is confirmed that there is no significant difference between a biosignal measured by a commercialized wet-type electrode according to the related art and a biosignal measured by a CNT composite electrode according to an exemplary embodiment. Thus, it may be understood that the CNT composite electrode according to an exemplary embodiment is used as an electrode for a biosignal.

Figure 4:
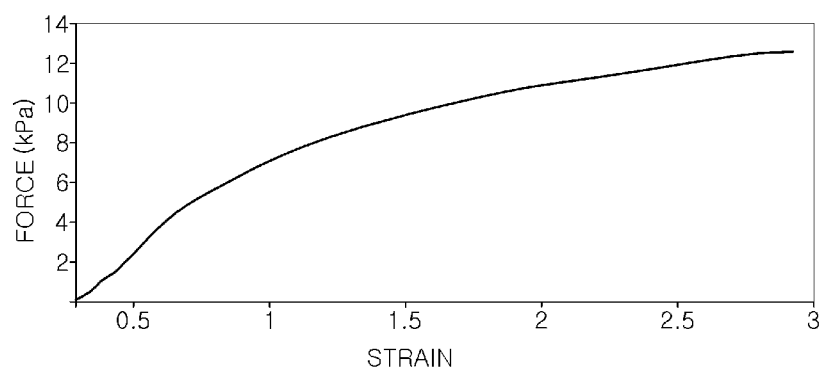
FIG. 4 illustrates data obtained by measuring an amount of force able to be withstood when a CNT composite electrode according to an exemplary embodiment is lifted vertically using a tensioner while the CNT composite electrode is attached to a subject.

FIG. 4 illustrates data obtained by measuring an amount of force to be withstood when the CNT composite electrode according to an exemplary embodiment is lifted vertically using a tensioner, while the CNT composite electrode is attached to a subject body.

As illustrated in FIG. 4, the CNT composite electrode according to an exemplary embodiment may withstand force up to 12 kPa. Thus, a biosignal may be accurately measured without dropping an electrode even during intense exercise.

As described above, an electrode is attached to the skin of a subject body via vacuum suction, so the electrode may be attached to the skin of a subject body without any tools or adhesives.

Moreover, according to an exemplary embodiment, a lower electrode includes a material such as aPDMS, so a space due to a wrinkle in the skin of a subject body may be significantly reduced. Thus, adhesion of an electrode may be maintained while skin troubles which occur during elongated measurement may be prevented.

The CNT composite electrode attached to the skin of a subject body via vacuum suction described above may be applied to a device for measuring a biosignal for an elongated period of time such as a holster, a wearable device, or the like.

As set forth above, according to an exemplary embodiment, an electrode is attached to the skin of a subject body via vacuum suction, so the electrode may be attached to the skin of a subject body without any tools or adhesives.

A lower electrode includes a material such as aPDMS, so a space due to a wrinkle in the skin of a subject body may be significantly reduced. Thus, adhesion of an electrode may be maintained while skin troubles which occur during elongated measurement may be prevented.

The CNT composite electrode attached to the skin of a subject body via vacuum suction described above may be applied to a device for measuring a biosignal for an elongated period of time such as a holster, a wearable device, or the like.

While exemplary embodiments have been shown and described above, it will be apparent to those skilled in the art that modifications and variations could be made without departing from the scope of the present invention as defined by the appended claims.

What is claimed is:

1. A Carbon NanoTube (CNT) composite electrode, comprising:
   a lower electrode having a through-hole formed therein, and configured to be attached to the skin of a subject body to detect a biosignal;
   an upper electrode provided on one surface of the lower electrode to form an enclosed space with respect to the lower electrode, and configured to receive the biosignal detected by the lower electrode; and
   an air discharge portion formed in at least one of the lower electrode and the upper electrode, and discharging air present in the enclosed space and the through-hole externally so as to be configured to allow the upper electrode and the lower electrode to be attached to the skin of the subject body via vacuum suction.

2. The CNT composite electrode of claim 1, wherein the upper electrode includes:
   an arcuate structure formed of a material having elastic force and restoring force;
   a conductive layer configured to be formed on an inner surface of the arcuate structure; and
   a snap connector formed on an outer surface of the arcuate structure, and configured to pass through the arcuate structure and to be connected to the conductive layer,
   wherein the lower electrode includes a circular plate-shaped structure formed of a material having adhesion and conductivity, and configured to be connected to the conductive layer, and
   wherein the through-hole is formed to pass through the circular plate-shaped structure.

3. The CNT composite electrode of claim 2, wherein the air discharge portion is formed on one side of the arcuate structure in contact with the circular plate-shaped structure, and is configured to be open when external force is applied and to be restored to an original state when the external force is removed.

4. The CNT composite electrode of claim 3, wherein the air discharge portion has a hinge structure.

5. The CNT composite electrode of claim 2, wherein the air discharge portion is formed on one surface of the circular plate-shaped structure attached to the skin of the subject body, and an outer portion of the air discharge portion protrudes while a central portion of the air discharge portion is concave.

6. The CNT composite electrode of claim 2, wherein the circular plate-shaped structure is formed of a mixed material of a Carbon NanoTube (CNT) and adhesive PolyDiMethylSiloane (aPDMS).

7. The CNT composite electrode of claim 2, wherein the conductive layer includes a conductor with which the entirety or a portion of the inner surface of the arcuate structure is coated using sputtering, or which is attached in the form of a conductive wire or a conductive tape.

8. The CNT composite electrode of claim 2, wherein one surface of the circular plate-shaped structure is further provided with an insulating layer for preventing the conductive layer of the upper electrode and the circular plate-shaped structure from being in contact with each other by the external force having been applied.

9. The CNT composite electrode of claim 1, wherein the through-hole and the air discharge portion are provided in an amount of at least two or more.

10. The CNT composite electrode of claim 2, wherein the material having elastic force and restoring force includes silicon.

* * * * *